US006367578B1

(12) United States Patent
Shoemaker

(10) Patent No.: US 6,367,578 B1
(45) Date of Patent: Apr. 9, 2002

(54) HEARING AID SOUND SEAL DEVICE

(76) Inventor: Howard E. Shoemaker, 4621 Chateau Dr., San Diego, CA (US) 92117

( * ) Notice: Subject to any disclaimer, the term of this patent is extended or adjusted under 35 U.S.C. 154(b) by 0 days.

(21) Appl. No.: 09/636,599

(22) Filed: Aug. 11, 2000

(51) Int. Cl.[7] .................................................. A61B 7/02

(52) U.S. Cl. ............................ 181/135; 84/129; 84/134

(58) Field of Search ................................ 181/135, 129, 181/134

(56) References Cited

U.S. PATENT DOCUMENTS

| | | | | | |
|---|---|---|---|---|---|
| 3,259,128 | A | * | 7/1966 | Leight et al. | 181/135 |
| D274,753 | S | | 7/1984 | Armstrong | |
| 4,459,247 | A | | 7/1984 | Rothemund | |
| 4,830,139 | A | * | 5/1989 | Circillo | 181/130 |
| 5,002,151 | A | * | 3/1991 | Olveira et al. | 181/130 |
| 5,044,463 | A | * | 9/1991 | Carr | 181/135 |
| 5,333,622 | A | | 8/1994 | Casali et al. | |
| 5,654,530 | A | * | 8/1997 | Sauer et al. | 181/130 |
| 5,682,020 | A | | 10/1997 | Oliveira | |
| 5,920,636 | A | * | 7/1999 | Olveira et al. | 381/328 |
| 6,006,857 | A | * | 12/1999 | Leight et al. | 181/135 |
| 6,082,485 | A | * | 7/2000 | Smith | 181/135 |

* cited by examiner

*Primary Examiner*—Robert E. Nappi
*Assistant Examiner*—Kim Lockett

(57) ABSTRACT

A hearing aid sound seal device for preventing audio feedback. The hearing aid sound seal device includes a support assembly being adapted to be securely and removably disposed about a hearing aid and being adapted to be snugly and removably received in an ear canal of a user's ear to essentially prevent audio feedback.

1 Claim, 2 Drawing Sheets

HEARING AID SOUND SEAL DEVICE

BACKGROUND OF THE INVENTION

1. Field of the Invention

The present invention relates to a sound seal for a hearing aid and more particularly pertains to a new hearing aid sound seal device for preventing audio feedback.

2. Description of the Prior Art

The use of a sound seal for a hearing aid is known in the prior art. More specifically, a sound seal for a hearing aid heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,920,636; U.S. Pat. No. 4,830,139; U.S. Pat. No. 5,682,020; U.S. Pat. No. 4,459,247; U.S. Pat. No. 5,333,622; and U.S. Pat. No. Des. 274,753.

While these devices fulfill their respective, particular objectives and requirements, the aforementioned patents do not disclose a new hearing aid sound seal device. The inventive device includes a support assembly being adapted to be securely and removably disposed about a hearing aid and being adapted to be snugly and removably received in an ear canal of a user's ear to essentially prevent sound from passing around the hearing aid.

In these respects, the hearing aid sound seal device according to the present invention substantially departs from the conventional concepts and designs of the prior art, and in so doing provides an apparatus primarily developed for the purpose of preventing audio feedback.

SUMMARY OF THE INVENTION

In view of the foregoing disadvantages inherent in the known types of sound seal for a hearing aid now present in the prior art, the present invention provides a new hearing aid sound seal device construction wherein the same can be utilized for preventing audio feedback.

The general purpose of the present invention, which will be described subsequently in greater detail, is to provide a new hearing aid sound seal device which has many of the advantages of the sound seal for a hearing aid mentioned heretofore and many novel features that result in a new hearing aid sound seal device which is not anticipated, rendered obvious, suggested, or even implied by any of the prior art sound seal for a hearing aid, either alone or in any combination thereof.

To attain this, the present invention generally comprises a support assembly being adapted to be securely and removably disposed about a hearing aid and being adapted to be snugly and removably received in an ear canal of a user's ear to essentially prevent sound from passing around the hearing aid.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new hearing aid sound seal device which has many of the advantages of the sound seal for a hearing aid mentioned heretofore and many novel features that result in a new hearing aid sound seal device which is not anticipated, rendered obvious, suggested, or even implied by any of the prior art sound seal for a hearing aid, either alone or in any combination thereof.

It is another object of the present invention to provide a new hearing aid sound seal device which may be easily and efficiently manufactured and marketed.

It is a further object of the present invention to provide a new hearing aid sound seal device which is of a durable and reliable construction.

An even further object of the present invention is to provide a new hearing aid sound seal device which is susceptible of a low cost of manufacture with regard to both materials and labor, and which accordingly is then susceptible of low prices of sale to the consuming public, thereby making such hearing aid sound seal device economically available to the buying public.

Still yet another object of the present invention is to provide a new hearing aid sound seal device which provides in the apparatuses and methods of the prior art some of the advantages thereof, while simultaneously overcoming some of the disadvantages normally associated therewith.

Still another object of the present invention is to provide a new hearing aid sound seal device for preventing audio feedback.

Yet another object of the present invention is to provide a new hearing aid sound seal device which includes a support assembly being adapted to be securely and removably disposed about a hearing aid and being adapted to be snugly and removably received in an ear canal of a user's ear to essentially prevent sound from passing around the hearing aid.

Still yet another object of the present invention is to provide a new hearing aid sound seal device that substantially prevents and blocks air from causing audio feedback in a user's ear canal.

Even still another object of the present invention is to provide a new hearing aid sound seal device that eliminates any distracting noises.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
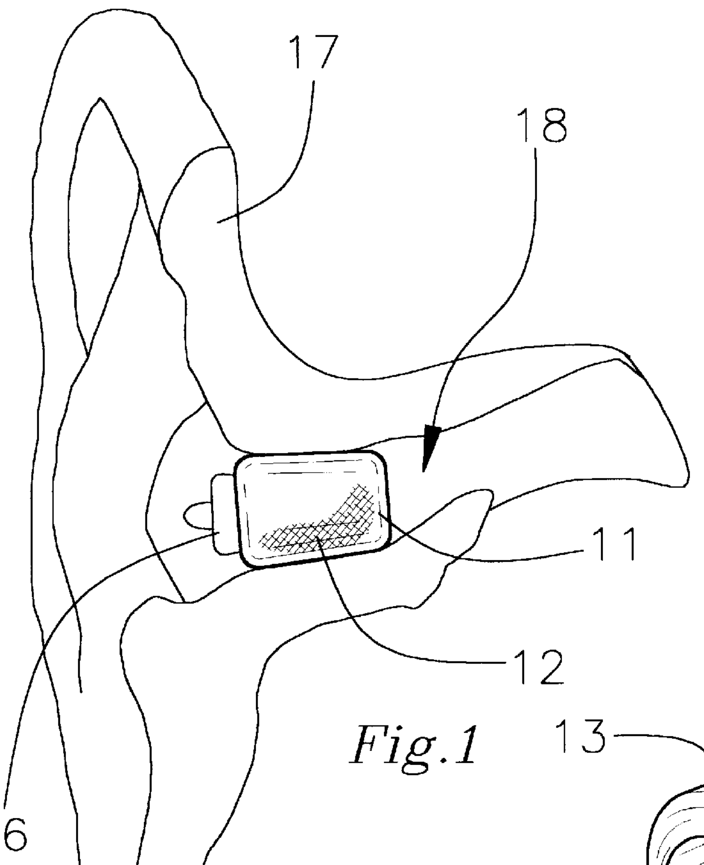
FIG. 1 is a perspective view of a first embodiment of a new hearing aid sound seal device according to the present invention shown in use.
Figure 2:
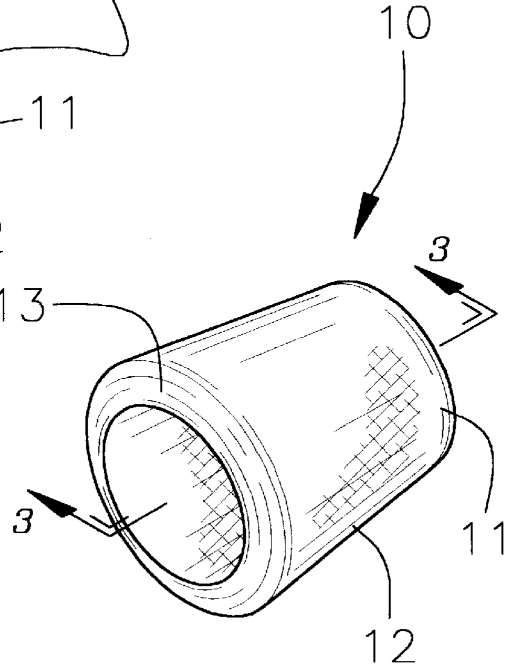
FIG. 2 is a perspective view of the first embodiment of the present invention.
Figure 3:
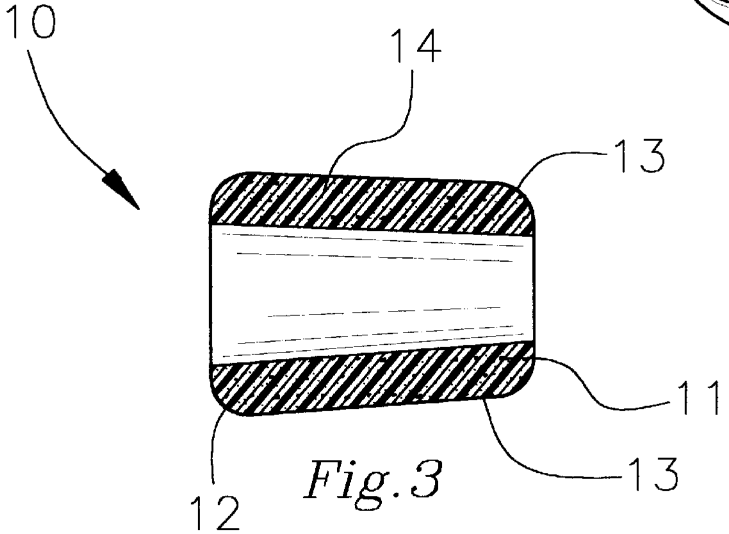
FIG. 3 is a cross-sectional view of the present invention.
Figure 4:
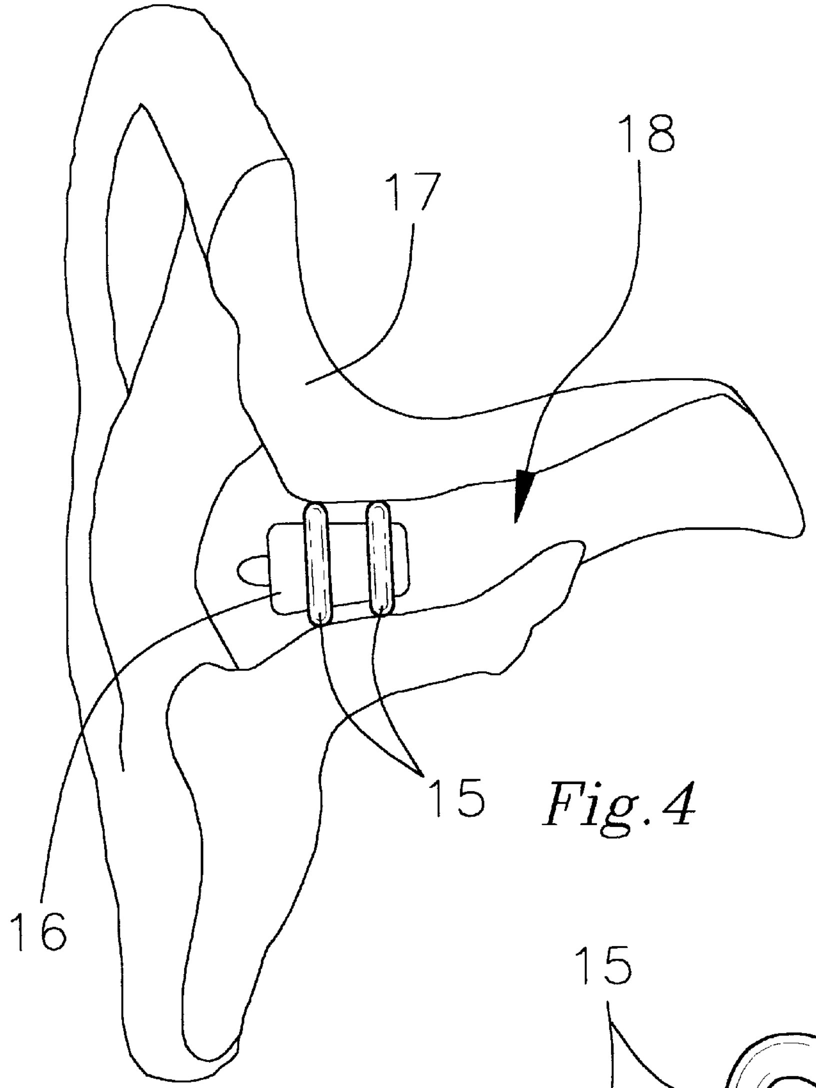
FIG. 4 is a perspective view of a second embodiment of the present invention.
Figure 5:
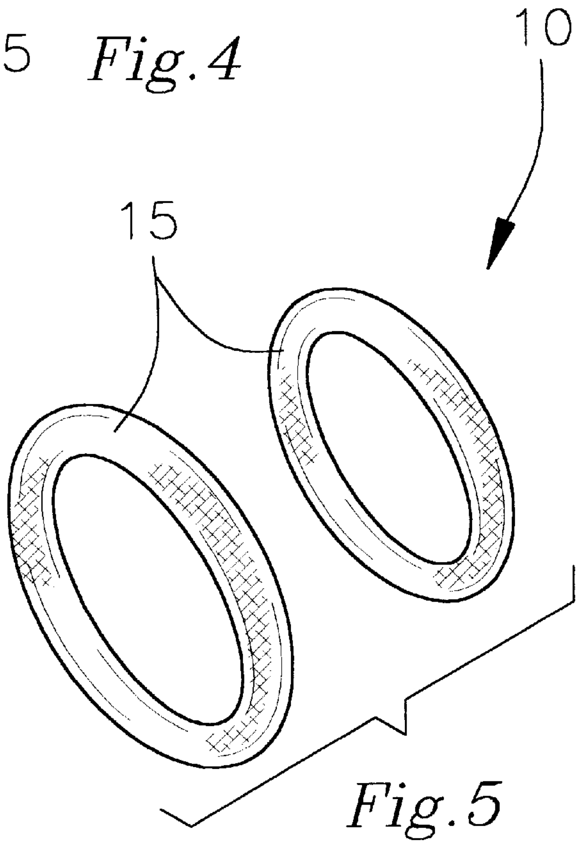
FIG. 5 is a perspective view of the second embodiment of the present invention.

With reference now to the drawings, and in particular to FIGS. 1 through 5 thereof, a new hearing aid sound seal device embodying the principles and concepts of the present invention and generally designated by the reference numeral 10 will be described.

As best illustrated in FIGS. 1 through 5, the hearing aid sound seal device 10 generally comprises a disposable support assembly 11 being adapted to be securely and removably disposed about a hearing aid 16 and being adapted to be snugly and removably received in an ear canal 18 of a user's ear 17 to essentially prevent sound from passing around the hearing aid 16. As a first embodiment, the support assembly 11 includes a pliable sleeve 12 which has a side wall 13 having a defined and consistent thickness throughout with the sleeve 12 being adapted to securely fit about the hearing aid 16. The side wall 13 of the sleeve 11 includes foam material 14 for providing a cushion to the user's ear canal 18 and to be able to fill the various contours of the user's ear canal 18 with the sleeve 11 being adapted to be removably engaged in the user's ear canal 18 to substantially prevent sound from passing around the hearing aid 16. The sleeve has a length of approximately ¼ to ½ inch.

As a second embodiment, the support assembly 1 includes one or more ring members 15 being adapted to be removably disposed about the hearing aid 16 and to be removably engaged in the user's ear canal 18 to substantially prevent sound from passing around the hearing aid 16 with each ring member 15 being essentially a pliable O-ring 15 which is made of a rubberized material for cushioning the user's ear canal 18 and also to fill the various contours found within the user's ear canal 18.

In use, the user places the support assembly 11 about the hearing aid 16 and then places the support assembly 11 and hearing aid 16 in the ear canal 18 of the user. The support assembly 11 is soft enough to be contorted in order to fill all the contours of the user's ear canal 18 in order to prevent sound from passing around the hearing aid 16.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hearing aid sound seal device comprising:

a support assembly being adapted to be securely and removably disposed about a hearing aid and being adapted to be snugly and removably received in an ear canal of a user's ear to essentially prevent sound from passing around the hearing aid;

wherein said support assembly includes a pair of ring members being adapted to be removably disposed about the hearing aid and to be removably engaged in the user's ear canal to substantially prevent sound from passing around the hearing aid, each of said ring members having a substantially circular cross-section taken in a plane extending along a radius of said at least one ring member;

wherein a first one of said ring members has an inner diameter being smaller than an inner diameter of a second one of said ring members.

* * * * *